(12) United States Patent
Tsubaki et al.

(10) Patent No.: US 8,934,703 B2
(45) Date of Patent: Jan. 13, 2015

(54) DETERMINATION ASSIST SYSTEM OF ULTRASONIC TESTING, DETERMINATION ASSIST METHOD OF ULTRASONIC TESTING, DETERMINATION ASSIST PROGRAM OF ULTRASONIC TESTING, AND COMPUTER-READABLE STORAGE MEDIUM FOR STORING DETERMINATION ASSIST PROGRAM OF ULTRASONIC TESTING

(75) Inventors: Kenji Tsubaki, Kakamigahara (JP); Katsumi Nagata, Kakamigahara (JP); Toshihiro Yamaoka, Ama-gun (JP); Hideyuki Hirasawa, Kobe (JP); Hironori Okauchi, Nishinomiya (JP)

(73) Assignee: Kawasaki Jukogyo Kabushiki Kaisha, Kobe-shi (JP)

( * ) Notice: Subject to any disclaimer, the term of this patent is extended or adjusted under 35 U.S.C. 154(b) by 154 days.

(21) Appl. No.: 13/497,201

(22) PCT Filed: Oct. 4, 2010

(86) PCT No.: PCT/JP2010/005932
§ 371 (c)(1),
(2), (4) Date: Jun. 8, 2012

(87) PCT Pub. No.: WO2011/043050
PCT Pub. Date: Apr. 14, 2011

(65) Prior Publication Data
US 2012/0250970 A1    Oct. 4, 2012

(30) Foreign Application Priority Data
Oct. 5, 2009   (JP) .................. 2009-231655

(51) Int. Cl.
*G06K 9/00* (2006.01)
*G01N 29/06* (2006.01)
*G01N 29/44* (2006.01)

(52) U.S. Cl.
CPC ........ *G01N 29/0654* (2013.01); *G01N 29/4427* (2013.01)
USPC .......................................... 382/141

(58) Field of Classification Search
None
See application file for complete search history.

(56) References Cited

U.S. PATENT DOCUMENTS 6,845,178 B1 * 1/2005 Evans et al. .................. 382/216
7,110,583 B2 * 9/2006 Yamauchi ..................... 382/128

(Continued)

FOREIGN PATENT DOCUMENTS

JP   A-59-075140    4/1984
JP   A-03-102258    4/1991

(Continued)

OTHER PUBLICATIONS

Grimberg et al. "Ultrasound and Visual Examination of Wood based Products" The 8th International Conference of the Slovenian Society for Non-Destructive Testing, Sep. 1-3, 2005, Portorož, Slovenia, pp. 109-115, hereinafter Grimberg.*

(Continued)

*Primary Examiner* — Jon Chang
*Assistant Examiner* — Oneal R Mistry
(74) *Attorney, Agent, or Firm* — Oliff PLC

(57) ABSTRACT

A determination assist system including a first image generating section for generating a first planar image based on data of a first test index; a second image generating section for generating a second planar image based on data of a second test index; a differentiation section which differentiates the first planar image and the second planar image to generate a first differential image and a second differential image, respectively; a binarization section which binarizes the first differential image to generate a first binary image including a first region which is not less than a first threshold and a second region which is less than the first threshold, and binarizes the second differential image to generate a second binary image including a third region which is not less than a second threshold and a fourth region which is less than the second threshold; and a determination image generating section.

17 Claims, 9 Drawing Sheets

(56) References Cited

U.S. PATENT DOCUMENTS

| | | | |
|---|---|---|---|
| 7,778,458 B2* | 8/2010 | Hiraoka | 382/141 |
| 7,804,993 B2* | 9/2010 | Dorphan et al. | 382/141 |
| 8,107,717 B2* | 1/2012 | Maeda et al. | 382/141 |
| 2002/0191831 A1* | 12/2002 | Spoto et al. | 382/141 |
| 2004/0066962 A1* | 4/2004 | Sasa et al. | 382/141 |
| 2005/0286753 A1* | 12/2005 | Ho | 382/141 |
| 2006/0184023 A1* | 8/2006 | Satoh | 600/437 |
| 2007/0206848 A1* | 9/2007 | Ohishi | 382/154 |
| 2007/0230768 A1* | 10/2007 | Adler et al. | 382/144 |
| 2008/0069429 A1* | 3/2008 | Choi et al. | 382/141 |
| 2008/0310700 A1* | 12/2008 | Fukusawa et al. | 382/141 |
| 2009/0128648 A1* | 5/2009 | Ikeda et al. | 348/222.1 |
| 2013/0251222 A1* | 9/2013 | Huang | 382/131 |

FOREIGN PATENT DOCUMENTS

| | | |
|---|---|---|
| JP | A-07-260751 | 10/1995 |
| JP | A-11-326580 | 11/1999 |
| JP | A-2005-031061 | 2/2005 |
| JP | A-2005-181170 | 7/2005 |
| WO | WO 2009/130140 A1 | 10/2009 |

OTHER PUBLICATIONS

Lines et al.; "Rapid Low-Cost, Full-Waveform Mapping and Analysis with Ultrasonic Arrays;" WCNDT—World Conference on NDT, 2004.

Gao et al.; "Scanning Acoustic Microscopy as a Tool for Quantitative Characterisation of Damage in CFRPs;" *Composites Science and Technology*; 1999, vol. 59, No. 3, pp. 345-354.

Arai et al.; "Large-Scale 3D Ultrasonic Inspection System;" *Toshiba Review*; 2007, vol. 62, No. 8, pp. 57-61. (with English-language abstract).

International Search Report issued in International Application No. PCT/JP2010/005932 Dated Oct. 26, 2010.

\* cited by examiner

|  | | BINARY C-TOF IMAGE | |
|---|---|---|---|
|  | | INDICATION (THIRD PIXEL) | NO INDICATION (FOURTH PIXEL) |
| BINARY C-AMP IMAGE | INDICATION (FIRST PIXEL) | DELAMINATION, VOID GREAT REFLECTION FOREIGN MATTER | POROSITY |
| | NO INDICATION (SECOND PIXEL) | SMALL REFLECTION FOREIGN MATTER | HEALTHY |

Fig.10

A: GENERAL PORTION (PLANE)
B: INCLINED PORTION OF BOTTOM SURFACE
C: ZERO POROSITY RATE SPECIFYING PORTION (MASK PORTION)
D: THICKNESS SPECIFYING PORTION

US 8,934,703 B2

DETERMINATION ASSIST SYSTEM OF ULTRASONIC TESTING, DETERMINATION ASSIST METHOD OF ULTRASONIC TESTING, DETERMINATION ASSIST PROGRAM OF ULTRASONIC TESTING, AND COMPUTER-READABLE STORAGE MEDIUM FOR STORING DETERMINATION ASSIST PROGRAM OF ULTRASONIC TESTING

TECHNICAL FIELD

The present invention relates to a determination assist system and a determination assist method of ultrasonic testing, which generate a determination image used to determine whether or not a composite material component is healthy, based on data relating to plural kinds of test indices obtained in an ultrasonic testing device. The present invention also relates to a determination assist program for causing a computer to perform the determination assist method, and a computer-readable storage medium for storing the determination assist program.

BACKGROUND ART

As an example of materials of components constituting aircraft, composite materials such as FRP are widely used. Also, an ultrasonic testing device is widely used to non-destructively test (inspect) internal flaws (cracks or defects) present in composite material components and to determine whether or not the components are healthy (flawless) (e.g., see Patent Literature 1).

In testing of flaws using the ultrasonic testing device, a probe generates an ultrasonic sound wave while the probe is moved along a surface of a composite material component to scan the composite material component. The generated ultrasonic sound wave travels through the interior of the composite material component and reaches a bottom surface of the composite material component or a flaw portion in the interior of the composite material component. The ultrasonic sound wave is reflected there and returns to the probe. The ultrasonic testing device obtains data relating to plural kinds of test indices such as intensity of the reflected sound wave and a time of flight (hereinafter referred to as "TOF") which passes from when the ultrasonic sound wave is generated until the reflected sound wave is received by the probe, based on the reception of the reflected sound wave in the probe.

The determination assist system generates determination images which visualize the interior of the composite material component based on these data. The determination images include, for example, a planar image (hereinafter referred to as "C-AMP image") which is a planar gradational image displayed according to the intensity of the reflected sound wave, a planar image (hereinafter referred to as "C-TOF image") which is a planar gradational image displayed according to a depth of a reflection source obtained based on TOF and a sound velocity, etc. An inspector identifies what kind of internal flaws are present and to what degree the internal flaws are present, in the composite material component, with reference to these plural images, and thereby determines whether or not the composite material component is healthy.

Non-patent Literature 1 discloses that a C-AMP image represented as a gray scale image and a C-TOF image represented as a color image are superposed together, to generate a determination image which is a color and gray-scale image.

CITATION LISTS

Patent Literature

Patent Literature 1: Japanese Laid-Open Patent Application Publication No. 2005-031061

Non-Patent Literature

Non-patent literature 1: D. Lines J. Skramstad, and R. Smith: "RAPID LOW-COST, FULL-WAVEFROM MAPPING AND ANALYSIS WITH ULTRASONIC ARRAYS", 16th WCN DT-World Conference on NDT (2004)

SUMMARY OF THE INVENTION

Technical Problem

However, the C-AMP image and the C-TOF image are gradational images. Therefore, if a flaw-like portion present in the composite material component is displayed by a predetermined gray scale, it is difficult to determine whether the flaw-like portion displayed by the predetermined gray scale (tone) is a flaw portion or a healthy portion.

It is considered that it is difficult to correctly identify the presence of internal flaws for composite material components based on the data obtained in the ultrasonic testing device, as compared to metal-made components. The internal flaws present in the composite material components include, for example, delamination, void, porosity, inclusion, etc. In general, regarding the porosity, a reflected signal from the flaw does not appear clearly, but the porosity is identified based on an amount of generation of the intensity of the reflected sound wave from the bottom surface of the composite material component. Therefore, it is difficult to identify the porosity with reference to the C-TOF image. The intensity of the reflected sound wave is differed depending on the kind of foreign matter included in the composite material component. Therefore, if a foreign matter which is low in intensity of the reflected sound wave is included in the composite material component, it is difficult to identify this foreign matter with reference to the C-AMP image. The delamination and the void tend to appear in both of the C-AMP image and the C-TOF image. Therefore, it can be estimated that based on the fact that a flaw-like portion appears in the same location of the two images that the delamination or the void is present in that location.

Under the circumstances, in the conventional method of determining whether or not the composite material component is healthy, the inspector is forced to visually check the C-AMP image and the C-TOF image which are gradational images, by checking them individually. To avert misdetection such as overlook of the internal flaws, the inspector is required to have high skill and sufficient experience.

It is difficult to classify the kind of the flaws or evaluate the flaws quantitatively, with reference to the determination image generated by the method disclosed in Non-patent Literature 1. The inspector is required to be experienced to correctly determine whether or not the composite material component is healthy. Even when the C-AMP image and the C-TOF image are binarized by setting thresholds, and the resulting binary images are combined to form a determination image, many false (fake) flaws are displayed due to the shape of the composite material component or for other reasons. Thus, it is not easy to find out genuine flaws.

Accordingly, an object of the present invention is to lessen an inspection burden required for ultrasonic testing of a composite material component and to make it possible to determine whether or not the composite material component is healthy, without depending on an inspector's skill.

Solution to Problem

The present invention has been made under the above mentioned circumstances, and a determination assist system for use in ultrasonic testing of the present invention, which generates a determination image used to determine whether or not a composite material component is healthy, based on data of plural kinds of test indices obtained in an ultrasonic testing device, comprises a first image generating section for generating a first planar image which is a gradational image, based on data of a first test index; a second image generating section for generating a second planar image which is a gradational image, based on data of a second test index; a differentiation section which differentiates the first planar image to generate a first differential image which is expressed as different tones corresponding to differential values, respectively, and differentiates the second planar image to generate a second differential image which is expressed as different tones corresponding to differential values, respectively; a binarization section which binarizes the first differential image to generate a first binary image including a first region which is not less than a first threshold and a second region which is less than the first threshold, and binarizes the second differential image to generate a second binary image including a third region which is not less than a second threshold and a fourth region which is less than the second threshold; and a determination image generating section which generates the determination image based on the first binary image and the second binary image.

A determination assist method for use in ultrasonic testing of the present invention, which generates a determination image used to determine whether or not a composite material component is healthy, based on data of plural kinds of test indices obtained in an ultrasonic testing device, comprises the steps of: generating a first planar image which is a gradational image, based on data of a first test index; generating a second planar image which is a gradational image, based on data of a second test index; differentiating the first planar image to generate a first differential image which is expressed as different tones corresponding to differential values, respectively, and differentiating the second planar image to generate a second differential image which is expressed as different tones corresponding to differential values, respectively; binarizing the first differential image to generate a first binary image including a first region which is not less than a first threshold and a second region which is less than the first threshold, and binarizing the second differential image to generate a second binary image including a third region which is not less than a second threshold and a fourth region which is less than the second threshold; and generating the determination image based on the first binary image and the second binary image.

A determination assist program for use in ultrasonic testing of the present invention is executed to cause a computer to perform the above method. A computer-readable storage medium of the present invention is configured to store the determination assist program.

In accordance with the above system, the above method, and the above program, an edge of an internal flaw which can be detected with reference to the first planar image appears as the first region in the first binary image, while other portion appears as the second region in the first binary image. In the same manner, the edge of the internal flaw appears as the third region in the second binary image, while other portion appears as the fourth region in the second binary image. Therefore, by setting the thresholds for binarization appropriately, an inspector can easily identify a flaw portion and a healthy portion in the composite material component.

Preferably, the determination image is generated in such a manner that the first binary image and the second binary image are superposed together, and in the determination image, a region where the first region and the third region overlap with each other, a region where the first region and the fourth region overlap with each other, a region where the second region and the third region overlap with each other, and a region where the second region and the fourth region overlap with each other can be identified such that the regions are distinguished from each other. Thus, in the determination image generated by superposing the first binary image and the second binary image together, it is possible to identify how the first region overlaps with the third and four regions and how the second region overlaps with the third and four regions. As a result, an edge of an internal flaw appearing in both of the first planar image and the second planar image, an edge of an internal flaw appearing only in the first planar image, an edge of an internal flaw appearing only in the second planar image, and a region of a healthy portion can be identified such that these regions are distinguished from each other, in one determination image.

For a component having a simple shape, for example, a shape in which its thickness is constant, a useful determination image can be obtained by combining an image generated by differentiating one of the first and second planar images and then binarizing the resulting differential image with an image generated by binarizing the other of the first and second planar images without differentiating it.

To generate a determination image used to determine whether or not porosity is present in a composite material component, among internal flaws of the composite material component, a method is advantageously used, which comprises the steps of: generating a first planar image which is a gradational image, based on data of signal intensity of a reflected sound wave; interpolating data of a thickness of a region of the composite material component for which a reflected sound wave from a bottom surface of the composite material component is not displayed in the first planar image, based on data of a thickness of a surrounding region of said region in the composite material component; and deriving a degree of the porosity based on the interpolated data of the thickness of said region, and a difference between signal intensity of a reflected sound wave from the bottom surface of the composite material component and signal intensity of a reflected sound wave from a portion where the porosity is present.

Advantageous Effects of the Invention

As described above, in accordance with the present invention, it is possible to lessen an inspection burden required for ultrasonic testing of a composite material component and to make it possible to determine whether or not the composite material component is healthy, without depending on an inspector's skill. The above object, other objects, features, and advantages of the present invention will be apparent by the following detailed description of preferred embodiments of the inventions, with reference to the accompanying drawings.

BRIEF DESCRIPTION OF THE DRAWINGS

FIG. 10 is a view showing the relation between display formats of the determination image of FIG. 9 and kinds of internal flaws.

EMBODIMENTS OF THE INVENTION

Figure 1:
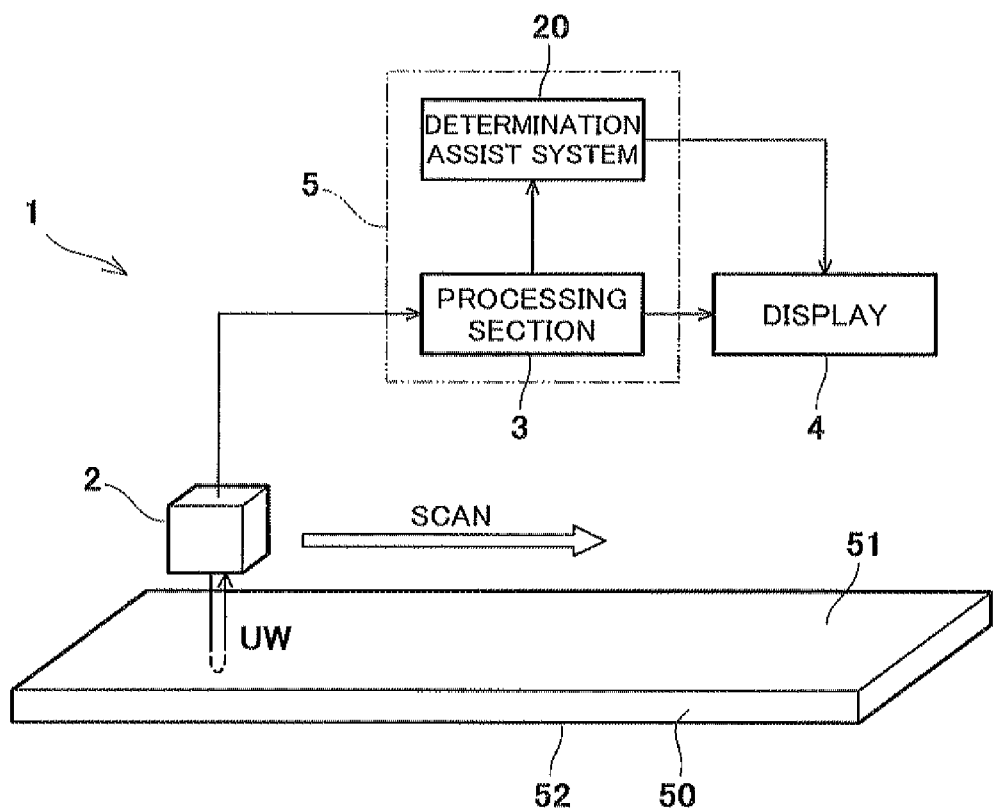
FIG. 1 is a view showing a configuration of an ultrasonic testing device according to an embodiment of the present invention.

Hereinafter, an embodiment of the present invention will be described with reference to the accompanying drawings. As shown in FIG. 1, an ultrasonic testing device 1 includes a probe 2 which generates an ultrasonic sound wave and receives a reflected sound wave, a processing section 3 which generates data for testing (inspection) based on the reflected sound wave received in the probe 2, and a display 4 which displays an image. The probe 2 may be an integrated one for generating the ultrasonic sound wave and receiving the reflected sound wave, or may be separately provided for generating the ultrasonic sound wave and receiving the reflected sound wave. The processing section 3 is one of functional blocks constituting a computer 5 as described later.

When ultrasonic testing of a composite material component 50 is conducted using the ultrasonic testing device 1, the probe 2 is moved along an upper surface 51 of the composite material component 50 to scan the composite material component 50. The probe 2 is moved within, for example, a plane parallel to the upper surface 51. During scanning, the probe 2 generates an ultrasonic sound wave in a direction from the upper surface 51 of the composite material component 50 toward a bottom surface 52 of the composite component 50 (see arrow UW). The generated ultrasonic sound wave travels through an interior of the composite material component 50 in a thickness direction thereof.

Figure 2:
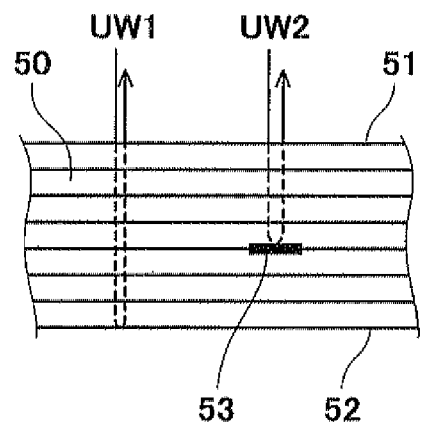
FIG. 2 is a conceptual view of ultrasonic testing using the ultrasonic testing device of FIG. 1.

As shown in FIG. 2, in general, if there are no flaws (defects) on a path through which the ultrasonic sound wave travels, the ultrasonic sound wave is reflected by the bottom surface 52 of the composite material component 50 (see arrow UW1). If a flaw 53 is present on the path, the ultrasonic sound wave is reflected by a portion where that flaw is present (see arrow UW2). The reflected sound wave travels through the interior of the composite material component 50 again toward the upper surface 51 in the thickness direction thereof, and is received in the probe 2 (see FIG. 1).

As shown in FIG. 1, the processing section 3 generates data relating to plural kinds of indices based on the reflected sound wave received in the probe 2. For example, the processing section 3 generates data of signal intensity (amplitude) of the reflected sound wave and data of TOF that passes from when the ultrasonic sound wave is generated until the reflected sound wave is received, for each scan position of the probe 2.

In some cases, there is a difference between signal intensity of the reflected sound wave from the flaw portion, and signal intensity of the reflected sound wave from the bottom surface 52. Therefore, with reference to data of the signal intensity for each scan position, it can be detected in which location an internal flaw is present within a scanned region. Since the ultrasonic sound wave is reflected by the flaw portion before it reaches the bottom surface, the TOF corresponding to the flaw portion is shorter than that corresponding to a healthy portion. Therefore, with reference to data of TOF for each scan position, it can be detected in which location the flaw portion is present within the scanned region. A travel distance of the ultrasonic sound wave can be derived from the TOF and a sound velocity. Therefore, it can be detected in which location the internal flaw is present in the thickness direction of the composite material component 50.

FRP which is a typical example of a composite material includes plate-shaped fibrous layers laminated together and bonded together. Examples of the internal flaws which may be present in the FRP are delamination, void, porosity, inclusion, etc. As described in the solution to problem, it is difficult to find out the porosity with reference to the data of the TOF, and it is difficult to find out the inclusion which is low in intensity of the reflected sound wave, with reference to the data of the signal intensity. It is difficult to accurately identify the internal flaws in the FRP. Therefore, in the embodiment of the present embodiment, the computer 5 including the processing section 3 is configured to incorporate a determination assist system 20 which generates a determination image used for identifying the kind and degree of the internal flaws.

Figure 3:
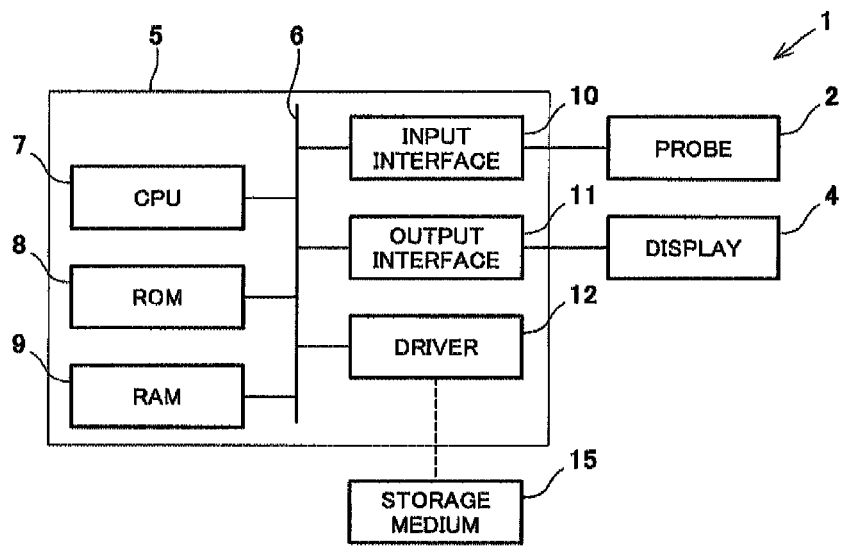
FIG. 3 is a block diagram showing a configuration of a computer of FIG. 1.

As shown in FIG. 3, the computer 5 includes a CPU 7, a ROM 8, RAMS, an input interface 10, an output interface 11, and a driver 12, which are interconnected via a bus 6. The probe 2 is coupled to the input interface 10. Information based on the reflected sound wave received in the probe 2 is input to the computer 5, and is stored in the RAM 9 as necessary. The display 4 is coupled to the output interface 11. Image information generated in the CPU 7 can be output from the computer 5 to the display 4. The display 4 is capable of displaying the image information from the computer 5.

The ROM 8 and the RAM 9 are configured to store programs to be executed by the CPU 7. Examples of such programs are a data generating program executed to appropriately process the input information from the probe 2 to acquire data of the signal intensity of the reflected sound wave and data of the TOF, for each scan position, a determination assist program executed to generate the above the determination image based on these data, etc.

A method of providing the determination assist program to the computer 5 is not particularly limited. The determination assist program may be provided to the computer 5 via an electric communication line (not shown) such as Internet, or the program provided in this way may be stored in a memory area according to a predetermined installation procedure. The computer 5 allows the driver 12 to read the programs stored in storage media 15 such as CD or DVD. Therefore, the determination assist program stored in the storage medium 15 can be stored in the memory area according to a predetermined installation procedure.

Figure 4:
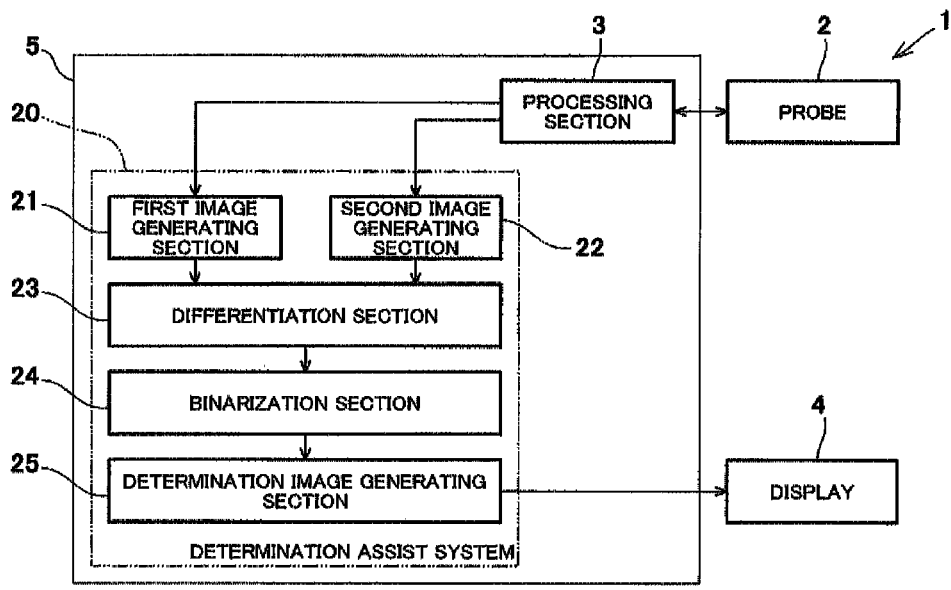
FIG. 4 is a functional block diagram showing a configuration of the computer of FIG. 3.

As shown in FIG. 4, the computer 5 includes the processing section 3 and the determination assist system 20 as the functional blocks which are able to execute the data generating program and the determination assist program. The determination assist system 20 includes a first image generating section 21, a second image generating section 22, a differentiation section 23, a binarization section 24, and a determination image processing section 25 as functional blocks based on a procedure content of the determination assist program. That is, the operation of each of the functional blocks 21 to 25 is equivalent to the content of each procedure commanded by the determination assist program.

Figure 5:
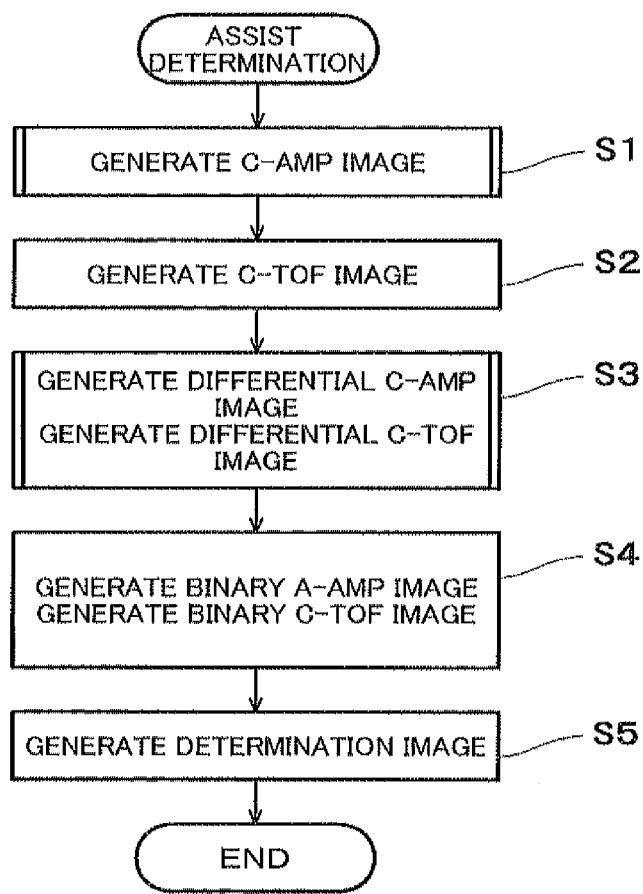
FIG. 5 is a flowchart showing a procedure of a determination assist program executed by the computer of FIG. 3.

Hereinafter, the procedure (i.e., determination assist method of the present invention) commanded by the determination assist program shown in FIG. 5 will be described. Initially, in step S1, the first image generating section 21 in the computer 5 generates "C-AMP image" based on the data of the signal intensity of the reflected sound wave for each scan position which is generated by the processing section 3. In step S2, the second image generating section 22 generates "C-TOF image" based on the data of the TOF for each scan position which is generated by the processing section 3. The order of step S1 and step S2 is not particularly limited.

Figure 6:
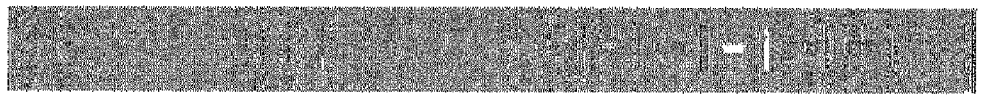
FIG. 6A is a view showing a C-AMP image generated by a first image generating section of FIG. 4.
FIG. 6B is a C-TOF image generated by a second image generating section of FIG. 4.
Figure 6A:
Figure 6B:
Figure 7A:
Figure 7B:

As illustrated in FIGS. 6A and 6B, the C-AMP image and the C-TOF image are planar images corresponding to a scan range of the probe, respectively. The C-AMP image and the C-TOF image are gradational images. Although white-black gradation is applied to the images in FIG. 6 as a form of gradation, another form (e.g., gradation of spectrum, etc.) may be applied to the image. In addition, the number of gray scales (tones) is not particularly limited.

The C-AMP image is generated in such a manner that a darker color is assigned to a pixel corresponding to each scan position, when the signal intensity of the corresponding reflected sound wave has a smaller value. This results in a planar gradational image as a whole. Typically, the signal intensity of the reflected sound wave is higher when the sound wave is reflected by the flaw portion than when the sound wave is reflected by the bottom surface, although it may depend on parameters used in inspection. With reference to the CAMP image, it may be estimated that some internal flaw is present in a scan position corresponding to a pixel assigned with a lighter color. By comparison, the C-TOF image is generated in such a manner that a darker color is assigned to a pixel corresponding to each scan position, when the corresponding TOF has a smaller value. This results in a planar gradational image as a whole. Typically, the TOF is shorter when the sound wave is reflected by the flaw portion than when the sound wave is reflected by the bottom surface. With reference to the C-TOF image, it may be estimated that some internal flaw is generated in a scan position corresponding to a pixel assigned with a darker color.

Then, in step S3, the differentiation section 23 differentiates the C-AMP image to generate "differential C-AMP image," and differentiates the C-TOF image to generate "differential C-TOF image."

Figure 7A:
FIG. 7A is a view showing a differential C-AMP image generated by a differentiation section of FIG. 4.
Figure 7B:
FIG. 7B is a view showing a differential C-TOF image generated by the differentiation section of FIG. 4.

As shown in FIGS. 7A and 7B, the differential C-AMP image and the differential C-TOF image are gradational images. The C-AMP differentiation image and the C-TOF differentiation image are each generated in such a manner that a darker color is assigned when a gradational change between adjacent pixels is greater. This results in planar gradational images as a whole. Therefore, roughly, in each of the differential C-AMP image and the differential C-TOF image, an edge of a region displayed as a lighter color in the corresponding original image, i.e., an edge of a region for which it is estimated that the internal flaw is present is displayed as a darker color.

Then, in step S4, the binarization section 24 binarizes the "differential C-AMP image" to generate "binary C-AMP image," and binarizes the differential C-TOF image to generate "binary C-TOF image."

Figure 8:
FIG. 8A is a view showing a binary CAMP image generated by a binarization section of FIG. 4.
FIG. 8B is a view showing a binary C-TOF image generated by the binarization section of FIG. 4.
Figure 8:

As shown in FIGS. 8A and 8B, each of the binary C-AMP image and the binary C-TOF image are generated in such a manner that it is determined whether or not a gray scale (tone) of each pixel in the corresponding differential image is not less than a threshold, and a pixel which is not less than the threshold and a pixel which is less than the threshold can be identified such that they are distinguished from each other. This results in planar images each of which is composed of two colors. Therefore, roughly, in the binary C-AMP image and the binary C-TOF image, clearer edges are displayed than in the corresponding differential images.

Then, in step S5, the determination image generating section 25 superposes the binary C-AMP image and the binary C-TOF image together, to generate the determination image. It is now assumed that a pixel which is determined as a pixel which is not less than a threshold, among pixels constituting the binary C-AMP image, is "first pixel," a pixel which is determined as a pixel which is less than the threshold, among pixels constituting the binary C-AMP image, is "second pixel," a pixel which is determined as a pixel which is not less than a threshold, among pixels constituting the binary C-TOF image, is "third pixel," and a pixel which is determined as a pixel which is less than the threshold, among pixels constituting the binary C-TOF image, is "fourth pixel."

Figure 9:
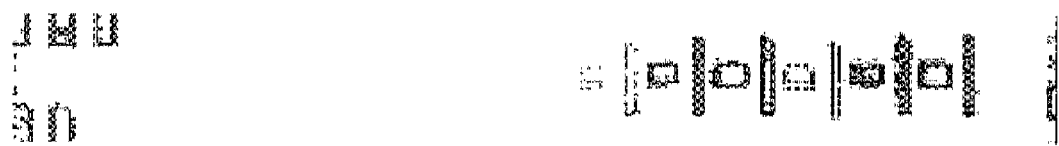
FIG. 9 is a view showing a determination image generated by a determination image generating section of FIG. 4.

As shown in FIG. 9, the determination image generating section 25 superposes the binary C-AMP image and the binary C-TOF image together, to generate the determination image in such a manner that a region where the first pixel of the binary C-AMP image and the third pixel of the binary C-TOF image overlap with each other, a region where the first pixel of the binary C-AMP image and the fourth pixel of the binary C-TOF image overlap with each other, a region where the second pixel of the binary C-AMP image and the third pixel of the binary C-TOF image overlap with each other, and a region where the second pixel of the binary C-AMP image and the fourth pixel of the binary C-TOF image overlap with each other, can be identified such that they are distinguished from each other.

The wordings "identified such that they are distinguished from each other" means that the above stated four regions are displayed by different colors, by different patterns, or in another way so that the inspector can easily visually distinguish these four regions when the determination image is displayed on the display 4.

FIG. 10 shows a correspondence among the four regions displayed to be identified such that they are distinguished from each other, and the kinds of the internal flaws of the composite material component 50.

In the region where the first and third pixels overlap with each other, the regions indicating the edges of the internal flaws in the two binary images overlap with each other. By identifying the region where the first and third pixels overlap with each other, the inspector can easily identify within this identified region, the delamination, the void, or the inclusion which is the presence of a foreign matter which is high in signal intensity of the reflected sound wave, among the internal flaws.

In the region where the first and fourth pixels overlap with each other, the region indicating the edge of the flaw portion in the binary C-AMP image and the region indicating the healthy portion in the binary C-TOF image overlap with each other. By identifying the region where the first and fourth pixels overlap with each other, the inspector can easily identify the porosity among the internal flaws, within this identified region.

In the region where the second and third pixels overlap with each other, the region indicating the healthy portion in the binary C-AMP image and the region indicating the edge of the flaw portion in the binary C-TOF image overlap with each other. By identifying the region where the second and third pixels overlap with each other, the inspector can easily identify within this identified region, the inclusion which is the presence of a foreign matter which is low in signal intensity of the reflected sound wave, among the internal flaws.

In the region where the second and fourth pixels overlap with each other, the regions indicating the healthy portions in the two binary images overlap with each other. By identifying the region where the second and fourth pixels overlap with each other, the inspector can easily identify this region as being healthy so long as this region is not a region located inward relative to any of the above stated three regions.

Thus, in accordance with the present embodiment, the kind of the internal flaws can be identified easily using one piece of determination image. Because of this, time required to identify the internal flaw can be reduced significantly, and an inspection burden of the ultrasonic testing can be lessened significantly. The determination image displays the edge of the internal flaw. Therefore, a planar area of the internal flaw can be derived easily, and how severe the internal flaw is can be identified easily for each kind of the internal flaws. This makes it possible to significantly lessen the inspection burden of the ultrasonic testing of the composite material structure, and determine whether or not the composite material component is healthy, without depending on the inspector's skill.

In the case of using the composite material such as FRP as a component of aircraft, the composite material component frequently has a non-uniform thickness. To change the thickness smoothly in such a composite material component, its upper surface and its bottom surface are not parallel in some cases. Because of this, when the probe is moved within a plane parallel to the upper surface to scan the composite material component, and generates the ultrasonic sound wave in a normal line direction of the upper surface, then the signal intensity of the reflected sound wave is low in a portion whose thickness changes, because the bottom surface is inclined with respect to the upper surface even though that portion is healthy. When the thickness is smaller, the TOF of even the healthy portion is shorter. In a case where the internal flaw is identified with reference to the binary C-AMP image and the binary C-TOF image, in a conventional method, the inspector must correctly determine whether gray scale (tone) display performed according to the signal intensity of the reflected sound wave or the TOF is due to a change in the thickness or presence of the internal flaw.

In the present embodiment, the determination image is generated after the C-AMP image and the C-TOF image have been subjected to the differentiation process and the binarization process. In a portion whose thickness changes smoothly, the corresponding signal intensity or TOF increases or decreases gradually, and therefore, a lighter color is assigned to this portion in the differential image. In the binarization process, proper thresholds are set to prevent the increase or decrease in the signal intensity or TOF due to such a thickness change from being extracted as the first pixel and the third pixel indicating the presence of the internal flaw. In this way, in the binary images, only the edge of the internal flaw can be extracted as the first and third pixels. Therefore, in the present embodiment, even when a composite material component whose thickness changes is tested, the internal flaw can be identified correctly.

For a component having a specific shape, for example, a shape in which its thickness change is small, a useful determination image can be generated by combining an image generated by binarizing the C-TOF image or the C-AMP image before differentiation, with the binary C-AMP image or the binary C-TOF image generated by binarizing the differential C-AMP image or the differential C-TOF image.

The probe 2 is moved in a range slightly wider than a range defined by an end of the upper surface 51 of the composite material component 50 in a state where the probe 2 faces the upper surface 51 of the composite material component 50, and transmits and receives the ultrasonic sound wave in a region outside the end of the composite material component 50. There is a difference in a value of the signal intensity of the reflected sound wave and a value of the TOF, between the outside region of the composite material component 50 and an inside region thereof. Therefore, if the C-AMP image and the C-TOF image are merely differentiated, a region in the vicinity of the end of the composite material component 50 is expressed as a darker color. As described above, the differential image of the present embodiment is generated to display the edge of the internal flaw clearly. But, if the internal flaw exists in the vicinity of the end, it is difficult to identify this. In the original planar images (i.e., C-AMP image and C-TOF image), a boundary line (i.e., end of the composite material component) between the inside region of the composite material component 50 and the outside region of the composite material component 50 appears according to a change in the value of the signal intensity of the reflected sound wave and a change in the value of the TOF.

Accordingly, preferably, in step S3, the differentiation section 23 generates each differential image in such a manner that the image generated by differentiating the original planar image is combined with a planar image newly created by setting a gate which captures only a signal of the reflected sound wave from the upper surface to determine presence/absence of a component in step S1, to make compensation so that a pixel expressed as the end of the composite material component in the original planar image is displayed as a lighter color. In this way, a pixel expressed as a darker color as corresponding to the end of the composite material component 50 is displayed as a lighter color, and only an internal flaw present in the vicinity of the end is displayed as a darker color. Therefore, by generating the determination image by using the compensated differential C-AMP image and the compensated differential C-TOF image, the internal flaw in the vicinity of the end can be identified correctly, with reference to the determination image.

Figure 11:
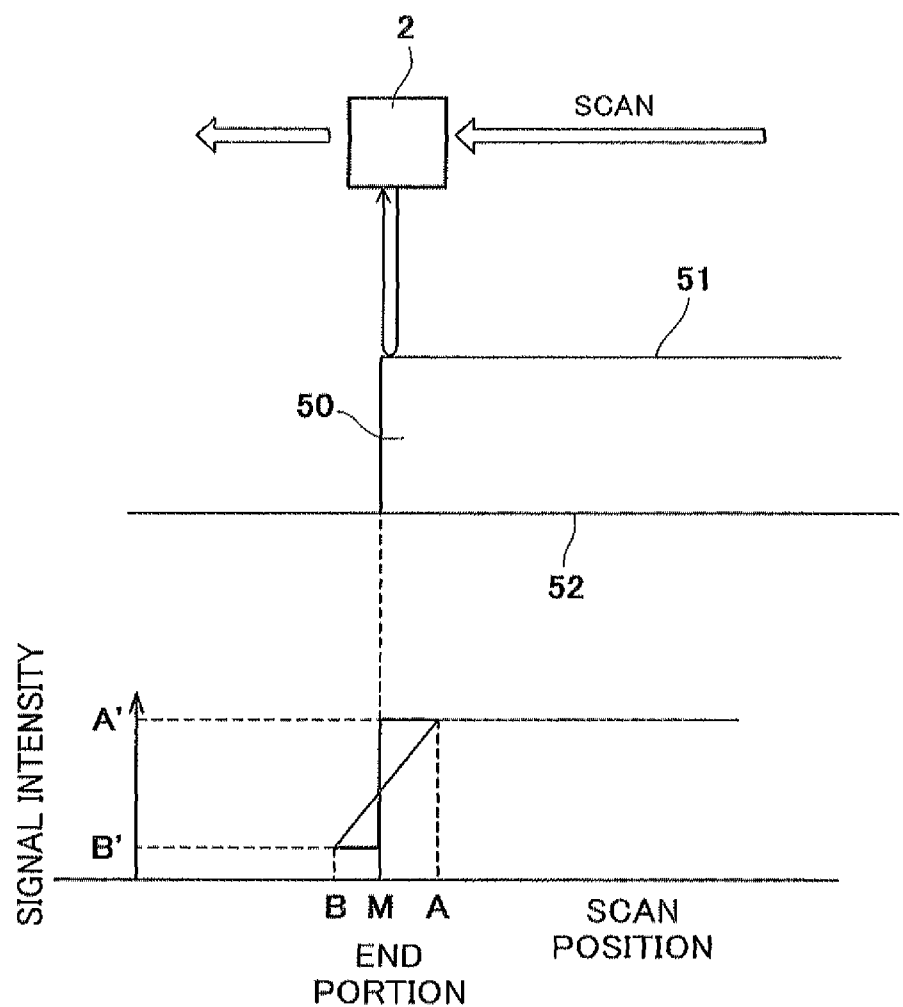
FIG. 11 is a conceptual view of a process for making compensation for data in the vicinity of an end which is performed by the first image generating section of FIG. 4.

As described above, a boundary line between the inside region of the composite material component 50 and the outside region of the composite material component 50 appears in the C-AMP image. In actuality, however, as shown in FIG. 11, the signal intensity of the reflected sound wave does not change sensitively, in the vicinity of the end. For this reason, in some cases, it is difficult to correctly identify the location of the end of the composite material component 50 with reference to the C-AMP image.

Accordingly, preferably, prior to step S2, the differentiation section 23 differentiates the C-AMP image in such a manner that compensation is made for the value of the signal intensity in the vicinity of the end so that the value of the signal intensity of the reflected sound wave changes sensitively at the boundary line which is the end of the composite material component 50, i.e., between the inside region of the composite material component 50 and the outside region of the composite material component 50. This compensation method is not particularly limited. An intermediate point M between a point A in the inside region at which a value A' of the signal intensity starts to change and a point B in the outside region at which a value B' of the signal intensity starts to change may be derived, and compensation may be made so that a value of signal intensity in a range from the point A to the intermediate point M becomes equal to the value A' of the signal intensity in the region inward relative to the point A. The C-AMP image generated after compensation is made in this way makes it possible to reduce a portion displayed as a darker color in a differential image, due to the end (in the present example, intermediate point M) of the composite material component, and improve a compensation accuracy of the differentiation image.

When the first image generating section 21 generates the C-AMP image in step S1, a gate may be set immediately below the upper surface to improve a resolution in the vicinity of the upper surface 51, in addition to the gate which captures the whole signal including the signal intensity of the sound wave reflected by the bottom surface 52. A planar image generated based on the gate added newly may be subjected to only the binarization process without the differentiation process, and the resulting image may be used to derive the determination image.

By performing the differentiation process or the binarization process on the planar image generated for each of the gates set in various ways, and considering each image, the location of the end can be identified correctly, and the determination image from which the internal flaw in the upper surface and in the vicinity of the bottom surface are extracted accurately can be generated.

Next, a procedure for accurately identifying the degree of the porosity will be described. As described above, the porosity might appear in the binary C-AMP image. Therefore, with reference to the determination image generated based on the binary CAMP image, the porosity can be identified.

Figure 12:
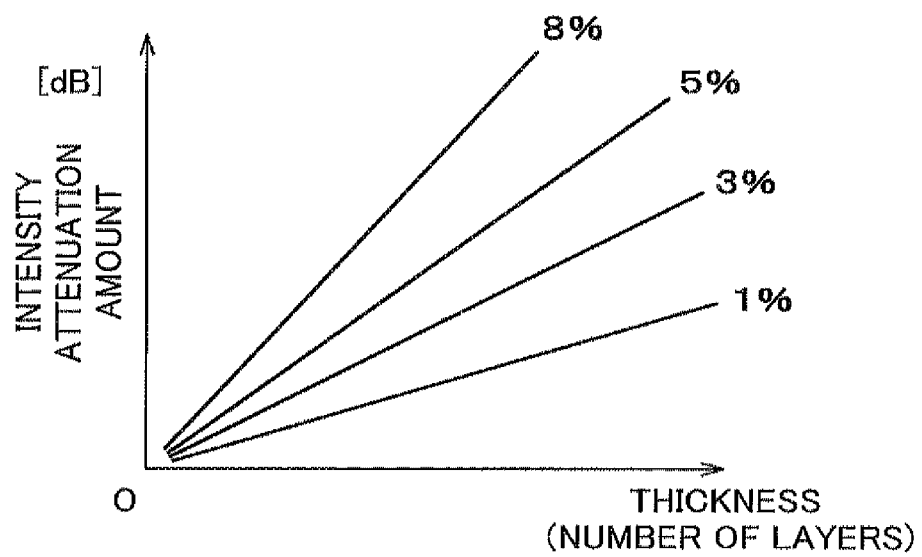
FIG. 12 is a porosity rate conversion graph stored in a memory area of FIG. 3.

Typically, the degree of porosity (hereinafter referred to as "porosity rate") is derived in such a manner that a difference between the signal intensity of the reflected sound wave from the bottom surface and the signal intensity of the reflected sound wave from a portion in which the porosity is present is calculated. Then, thickness information is obtained from the C-TOF image. Then, with reference to a porosity rate conversion graph shown in FIG. 12, the porosity rate is derived based on the difference in signal intensity and the thickness (or the number of layers) of the composite material component.

However, if the porosity rate is not lower than a certain level, the reflected sound wave from the bottom surface cannot be acquired as a clear one, and thickness information of this portion cannot be acquired surely. Hereinafter, the portion from which the reflected sound wave from the bottom surface cannot be acquired as a clear one is referred to as "portion from which no reflected signal is obtained from the bottom surface."

Based on the thickness information obtained from the healthy portion in the vicinity of the portion from which no reflected signal is obtained from the bottom surface, the thickness of the portion from which no reflected signal is obtained from the bottom surface is derived by interpolation. Based on the thickness information derived by the interpolation and the difference in the signal intensity, and with reference to the porosity rate conversion graph, the porosity rate is derived. The interpolation process allows the porosity rate to be identified correctly even when a level of the porosity rate is high. Thus, it can be determined whether or not the composite material component is healthy.

As described above, the composite material component for use in aircraft often has a portion whose thickness changes. If the portion from which no reflected signal is obtained from the bottom surface is formed in the portion whose thickness changes, an interpolated portion of the bottom surface is preferably inclined with respect to the upper surface like the surrounding portion of the bottom surface. Thus, even when the portion from which no reflected signal is obtained from the bottom surface is formed in the portion whose thicknesses changes, the porosity rate can be identified correctly.

Figure 13:
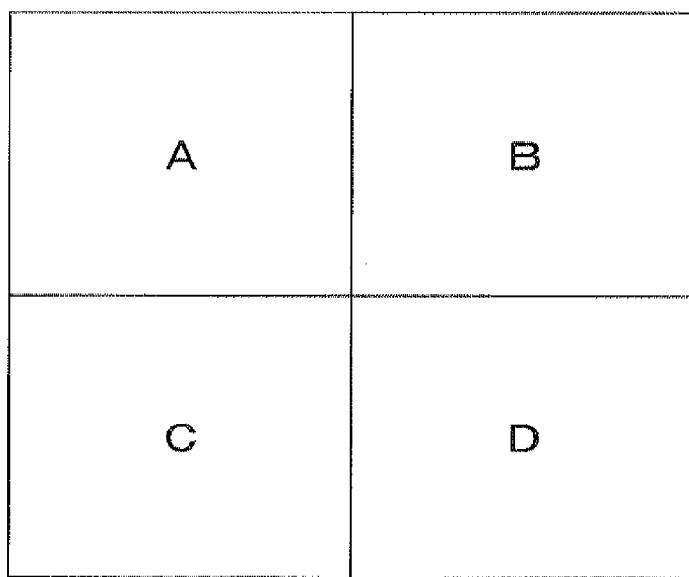
FIG. 13 is a testing condition application map stored in a memory area of FIG. 3.

In the portion whose thickness changes, the bottom surface is not parallel to the upper surface. In this portion, the intensity of the reflected signal is lower than that of a portion in which the bottom surface is parallel to the upper surface even if these portions are equal in thickness. In order to address such a case where the bottom surface is inclined with respect to the upper surface, different porosity rate conversion graphs are preferably utilized depending on the inclination angle of the bottom surface of the composite material component with respect to its upper surface. This makes it possible to derive the porosity rate correctly even in cases where a certain composite material component includes different structures or shapes. Note that the porosity rate conversion graph set for each portion may include a graph used for deriving zero as the porosity rate irrespective of a thickness difference and a signal difference. This graph applied to a predetermined portion can serve as a mask which prevents the porosity rate from being evaluated for the predetermined portion. To automatically select a conversion graph from among these plural conversion graphs, a test condition application map is used (see FIG. 13).

Figure 14:
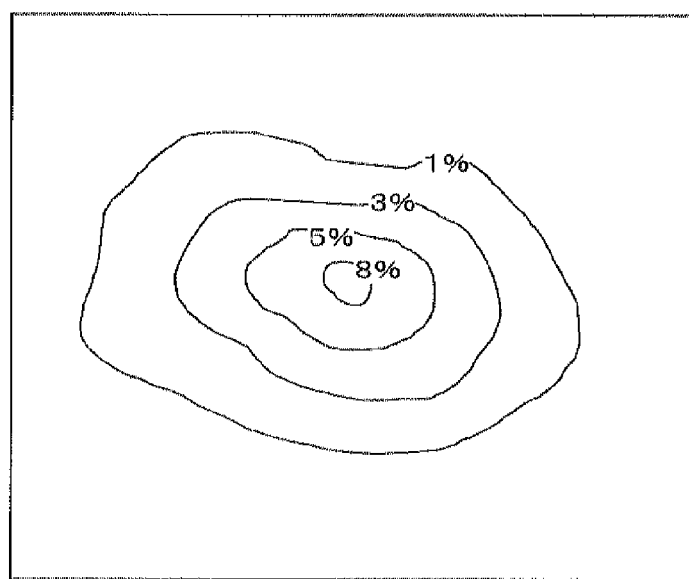
FIG. 14 is an example of a contour representation showing a magnitude of the porosity rate.

In order to address a case where evaluation based on a particular thickness is necessary, a thickness map may be pre-stored in a memory area, instead of thickness information derived from the C-TOF image. Alternatively, the thickness map may be contained in the test condition application map. In a further alternative, a planar image may be generated in such a manner that the planar image is displayed by gray scales (tones) according to the porosity rate. In this planar image, a magnitude of the porosity rate can be displayed as a contour representation shown in FIG. 14. In a further alternative, the planar image displayed as the contour representation and the C-AMP image may be superposed together.

Although the embodiment of the present invention has been described, the embodiment of the present invention can be suitably changed within the scope of the present invention.

INDUSTRIAL APPLICABILITY

In accordance with the present invention, it is possible to achieve advantages that a burden of a work for determining whether or not an internal flaw is present in a composite material component can be lessened and determination can be made substantially without depending on an inspector's skill. Therefore, the present invention is advantageously applied to ultrasonic testing of large-sized components such as composite material components for use in aircraft.

REFERENCE SIGNS LISTS 1 ultrasonic testing device
5 computer
7 CPU
8 ROM
9 RAM
12 driver
15 storage medium
20 determination assist system
21 first image generating section
22 second image generating section
23 differentiation section
24 binarization section
25 determination image generating section

The invention claimed is:

1. A determination assist system for use in ultrasonic testing, which generates a determination image used to determine whether or not a composite material component is healthy, based on data of plural kinds of test indices obtained in an ultrasonic testing device, the determination assist system comprising:
   a first image generating section for generating a first planar image which is a gradational image, based on data of a signal intensity of a reflected sound wave as a first test index;
   a second image generating section for generating a second planar image which is a gradational image, based on data of a propagation time of an ultrasonic sound wave as a second test index;
   a differentiation section which differentiates the first planar image to generate a first differential image which is expressed as different tones corresponding to differential values, respectively, and differentiates the second planar image to generate a second differential image which is expressed as different tones corresponding to differential values, respectively;
   a binarization section which binarizes the first differential image to generate a first binary image including a first region which is not less than a first threshold and a second region which is less than the first threshold, and binarizes the second differential image to generate a second binary image including a third region which is not less than a second threshold and a fourth region which is less than the second threshold; and
   a determination image generating section which generates the determination image based on the first binary image and the second binary image,
   wherein the determination image generating section generates the determination image by superposing the first binary image and the second binary image in such a manner that a fifth region where the first region and the third region overlap, a sixth region where the first region and the fourth region overlap, a seventh region where the second region and the third region overlap, and an eighth region where the second region and the fourth region overlap can be distinguished from each other.

2. The determination assist system for use in ultrasonic testing according to claim 1,
   wherein the first image generating section generates the first planar image after compensation is made to cause the data of the first test index in an end portion of the composite material component to change sensitively.

3. The determination assist system for use in ultrasonic testing according to claim 1, further comprising:
   a third image generating section for generating a third planar image which is a gradational image, based on data of a third test index; and
   a compensation section which makes compensation for the first differential image to generate a compensated first differential image in such a manner that the first differential image and the third planar image are superposed together to cancel a higher differential value generated in an end portion of the composite material component from the first differential image;
   wherein the binarization section generates the first binary image based on the compensated first differential image.

4. The determination assist system for use in ultrasonic testing according to claim 3,
   wherein the third test index is a signal intensity of a reflected sound wave.

5. A determination assist system for use in ultrasonic testing, which generates a determination image used to determine whether or not a composite material component is healthy, based on data of plural kinds of test indices obtained in an ultrasonic testing device, the determination assist system comprising:
   a first image generating section for generating a first planar image which is a gradational image, based on data of a signal intensity of a reflected sound wave as a first test index;
   a second image generating section for generating a second planar image which is a gradational image, based on data of a propagation time of an ultrasonic sound wave as a second test index;
   a differentiation section which differentiates one of the first planar image and the second planar image to generate a differential image which is expressed as different tones corresponding to differential values, respectively;
   a binarization section which binarizes the differential image to generate a first binary image including a first region which is not less than a first threshold and a second region which is less than the first threshold, and binarizes the one of the first planar image and the second planar image which was not differentiated to generate a second binary image including a third region which is not less than a second threshold and a fourth region which is less than the second threshold; and
   a determination image generating section which generates the determination image based on the first binary image and the second binary image,
   wherein the determination image generating section generates the determination image by superposing the first binary image and the second binary image in such a manner that a fifth region where the first region and the third region overlap, a sixth region where the first region and the fourth region overlap, a seventh region where the second region and the third region overlap, and an eighth region where the second region and the fourth region overlap can be distinguished from each other.

6. The determination assist system for use in ultrasonic testing according to claim 5, wherein the first image generating section generates the first planar image after compensation is made to cause the data of the first test index in an end portion of the composite material component to change sensitively.

7. The determination assist system for use in ultrasonic testing according to claim 5, further comprising:
- a third image generating section for generating a third planar image which is a gradational image, based on data of a third test index; and
- a compensation section which makes compensation for the differential image to generate a compensated differential image in such a manner that the differential image and the third planar image are superposed together to cancel a higher differential value generated in an end portion of the composite material component from the differential image;
- wherein the binarization section generates the first binary image based on the compensated differential image.

8. The determination assist system for use in ultrasonic testing according to claim 7, wherein the third test index is a signal intensity of a reflected sound wave.

9. A determination assist method for use in ultrasonic testing, which generates a determination image used to determine whether or not a composite material component is healthy, based on data of plural kinds of test indices obtained in an ultrasonic testing device, the determination assist method comprising the steps of:
- generating a first planar image which is a gradational image, based on data of a signal intensity of a reflected sound wave as a first test index;
- generating a second planar image which is a gradational image, based on data of a propagation time of an ultrasonic sound wave as a second test index;
- differentiating the first planar image to generate a first differential image which is expressed as different tones corresponding to differential values, respectively, and differentiating the second planar image to generate a second differential image which is expressed as different tones corresponding to differential values, respectively;
- binarizing the first differential image to generate a first binary image including a first region which is not less than a first threshold and a second region which is less than the first threshold, and binarizing the second differential image to generate a second binary image including a third region which is not less than a second threshold and a fourth region which is less than the second threshold; and
- generating the determination image by superposing the first binary image and the second binary image in such a manner that a fifth region where the first region and the third region overlap, a sixth region where the first region and the fourth region overlap, a seventh region where the second region and the third region overlap, and an eighth region where the second region and the fourth region overlap can be distinguished from each other.

10. The determination assist method for use in ultrasonic testing according to claim 9, wherein in the step of generating the first planar image, the first planar image is generated after compensation is made to cause the data of the first test index in an end portion of the composite material component to change sensitively.

11. The determination assist method for use in ultrasonic testing according to claim 9, wherein the step of generating the first differential image and the second differential image includes:
- generating a third planar image which is a gradational image, based on data of a third test index; and
- making compensation for the first differential image to generate a compensated first differential image in such a manner that the first differential image and the third planar image are superposed together to cancel a higher differential value generated in an end portion of the composite material component from the first differential image,
- wherein in the step of generating the first binary image and the second binary image, the first binary image is generated based on the compensated first differential image.

12. The determination assist method for use in ultrasonic testing according to claim 11, wherein the third test index is a signal intensity of a reflected sound wave.

13. A determination assist method for use in ultrasonic testing, which generates a determination image used to determine whether or not a composite material component is healthy, based on data of plural kinds of test indices obtained in an ultrasonic testing device, the determination assist method comprising the steps of:
- generating a first planar image which is a gradational image, based on data of a signal intensity of a reflected sound wave as a first test index;
- generating a second planar image which is a gradational image, based on data of a propagation time of an ultrasonic wave as a second test index;
- differentiating one of the first planar image and the second planar image to generate a differential image which is expressed as different tones corresponding to differential values, respectively;
- binarizing the differential image to generate a first binary image including a first region which is not less than a first threshold and a second region which is less than the first threshold, and binarizing the one of the first planar image and the second planar image which was not differentiated to generate a second binary image including a third region which is not less than a second threshold and a fourth region which is less than the second threshold; and
- generating the determination image by superposing the first binary image and the second binary image in such a manner that a fifth region where the first region and the third region overlap, a sixth region where the first region and the fourth region overlap, a seventh region where the second region and the third region overlap, and an eighth region where the second region and the fourth region overlap can be distinguished from each other.

14. The determination assist method for use in ultrasonic testing according to claim 13, wherein in the step of generating the first planar image, the first planar image is generated after compensation is made to cause the data of the first test index in an end portion of the composite material component to change sensitively.

15. The determination assist method for use in ultrasonic testing according to claim 13, wherein the step of generating the differential image includes:
- generating a third planar image which is a gradational image, based on data of a third test index; and
- making compensation for the differential image to generate a compensated differential image in such a manner that the differential image and the third planar image are superposed together to cancel a higher differential value generated in an end portion of the composite material component from the differential image,
- wherein in the step of generating the first binary image and the second binary image, the first binary image is generated based on the compensated differential image.

16. The determination assist method for use in ultrasonic testing according to claim 15, wherein the third test index is a signal intensity of a reflected sound wave.

17. A non-transitory computer-readable storage medium that stores a determination assist program that generates a determination image used to determine whether or not a composite material component is healthy, based on data of plural kinds of test indices obtained in an ultrasonic testing device, the program comprising:

instructions for generating a first planar image which is a gradational image, based on data of a signal intensity of a reflected sound wave as a first test index;

instructions for generating a second planar image which is a gradational image, based on data of a propagation time of an ultrasonic sound wave as a second test index;

instructions for differentiating the first planar image to generate a first differential image which is expressed as different tones corresponding to differential values, respectively, and differentiating the second planar image to generate a second differential image which is expressed as different tones corresponding to differential values, respectively;

instructions for binarizing the first differential image to generate a first binary image including a first region which is not less than a first threshold and a second region which is less than the first threshold, and binarizing the second differential image to generate a second binary image including a third region which is not less than a second threshold and a fourth region which is less than the second threshold; and instructions for generating the determination image by superposing the first binary image and the second binary image in such a manner that a fifth region where the first region and the third region overlap, a sixth region where the first region and the fourth region overlap, a seventh region where the second region and the third region overlap, and an eighth region where the second region and the fourth region overlap can be distinguished from each other.

* * * * *

UNITED STATES PATENT AND TRADEMARK OFFICE
CERTIFICATE OF CORRECTION

PATENT NO. : 8,934,703 B2
APPLICATION NO. : 13/497201
DATED : January 13, 2015
INVENTOR(S) : Kenji Tsubaki et al.

Page 1 of 2

Figure 7C:
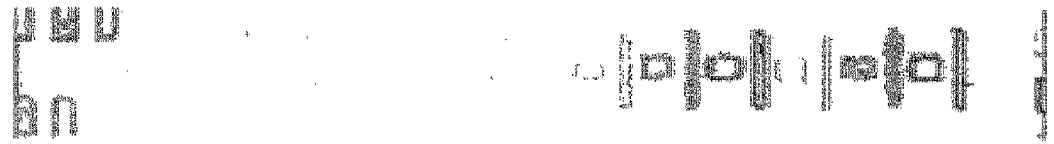

It is certified that error appears in the above-identified patent and that said Letters Patent is hereby corrected as shown below:

The attached replacement drawing sheet replaces FIG. 6-7C in the original sheet with FIGS. 6A-7B in the attached Replacement Sheet.

Signed and Sealed this
Nineteenth Day of April, 2016

Michelle K. Lee
*Director of the United States Patent and Trademark Office*